(12) United States Patent
Mistretta

(10) Patent No.: US 6,954,067 B2
(45) Date of Patent: Oct. 11, 2005

(54) THREE-DIMENSIONAL PHASE CONTRAST IMAGING USING INTERLEAVED PROJECTION DATA

(75) Inventor: Charles A. Mistretta, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 10/290,735

(22) Filed: Nov. 8, 2002

(65) Prior Publication Data

US 2003/0135103 A1 Jul. 17, 2003

Related U.S. Application Data

(60) Provisional application No. 60/339,076, filed on Nov. 12, 2001.

(51) Int. Cl.[7] .................................................. G01V 3/00
(52) U.S. Cl. ...................................................... 324/307
(58) Field of Search ................................. 324/307, 309, 324/300, 306; 600/410

(56) References Cited

U.S. PATENT DOCUMENTS

| | | | | |
|---|---|---|---|---|
| 5,225,779 A | * | 7/1993 | Parker et al. | 324/306 |
| 5,233,298 A | * | 8/1993 | Dumoulin | 324/306 |
| 5,929,637 A | * | 7/1999 | Taguchi et al. | 324/306 |
| 6,031,374 A | * | 2/2000 | Epstein et al. | 324/306 |
| 6,163,152 A | * | 12/2000 | Bernstein et al. | 324/306 |
| 6,188,922 B1 | | 2/2001 | Mistretta et al. | |
| 6,393,313 B1 | * | 5/2002 | Foo | 600/410 |
| 6,487,435 B2 | * | 11/2002 | Mistretta et al. | 600/420 |
| 2001/0027262 A1 | | 10/2001 | Mistretta et al. | |

OTHER PUBLICATIONS

Gu, T., et al. "Phase contrast 3D flow spectrum acquisition using VIPR." Proc. Intl. Soc. Mag. Reson. Med. 10, 2002, p. 1799.

Barger, A.V.; et al. "Phase–Contrast With Interleaved Under-sampled Projections." Magnetic Resonance in Medicine 43, 2002, pp. 503–509.

Wendt III, Richard E., et al. "Nuclear Magnetic Resonance Velocity Spectra of Pulsatile Flow in a Rigid Tube." Academic Press, Inc., 1992, pp. 214–225.

Barger, A.V., et al. "3D Multiphase Coronary Artery Imaging in a Single Breath–hold using Undersampled Projection Reconstruction." Proc. Intl. Soc. Mag. Reson. Med. 8, 2000 p. 1513.

* cited by examiner

Primary Examiner—Louis Arana
Assistant Examiner—Dixomara Vargas
(74) Attorney, Agent, or Firm—Quarles & Brady LLP

(57) ABSTRACT

A three dimensional projection reconstruction pulse sequence is employed to acquire velocity encoded NMR data from which an image indicative of spin motion is reconstructed. The velocity encoding is along all three axes and it may include acquisitions at more than one velocity encoding first moment M1. When more than one first moment M1 is acquired, a 1DFT along the velocity encoding axis is performed prior to reconstructing images from the acquired NMR data.

11 Claims, 9 Drawing Sheets

THREE-DIMENSIONAL PHASE CONTRAST IMAGING USING INTERLEAVED PROJECTION DATA

CROSS-REFERENCE TO RELATED APPLICATIONS

This application claims the benefit of U.S. Provisional patent application Ser. No. 60/339,076 filed on Nov. 12, 2001 and entitled "THREE-DIMENSIONAL PHASE CONTRAST IMAGING USING INTERLEAVED PROJECTION DATA".

STATEMENT REGARDING FEDERALLY SPONSORED RESEARCH

This invention was made with government support under Grant No. HL62425 awarded by the National Institute of Health. The United States Government has certain rights in this invention.

BACKGROUND OF THE INVENTION

The field of the invention is nuclear magnetic resonance ("NMR") imaging methods and systems. More particularly, the invention relates to the acquisition of NMR images indicative of flow, or motion.

When a substance such as human tissue is subjected to a uniform magnetic field (polarizing field B0), the individual magnetic moments of the spins in the tissue attempt to align with this polarizing field, but precess about it in random order at their characteristic Larmor frequency. If the substance, or tissue, is subjected to a magnetic field (excitation field B1) which is in the x-y plane and which is near the Larmor frequency, the net aligned moment, Mz, may be rotated, or "tipped", into the x-y plane to produce a net transverse magnetic moment Mt. A signal is emitted by the excited spins after the excitation signal B1 is terminated, this signal may be received and processed to form an image.

When utilizing these signals to produce images, magnetic field gradients (Gx Gy and Gz) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

The prevailing methods used to acquire NMR signals and reconstruct images use a variant of the well known Fourier transform (FT) imaging technique, which is frequently referred to as "spin-warp". The spin-warp technique is discussed in an article entitled "Spin-Warp NMR Imaging and Applications to Human Whole-Body Imaging" by W. A. Edelstein et al., Physics in Medicine and Biology, Vol. 25, pp. 751–756 (1980). It employs a variable amplitude phase encoding magnetic field gradient pulse prior to the acquisition of NMR spin-echo signals to phase encode spatial information in the direction of this gradient. In a two-dimensional implementation (2DFT), for example, spatial information is encoded in one direction by applying a phase encoding gradient (Gy) along that direction, and then a spin-echo signal is acquired in the presence of a readout magnetic field gradient (Gx) in a direction orthogonal to the phase encoding direction. The readout gradient present during the spin-echo acquisition encodes spatial information in the orthogonal direction. In a typical 2DFT pulse sequence, the magnitude of the phase encoding gradient pulse Gy is incremented ($\Delta$Gy) in the sequence of views that are acquired during the scan to produce a set of NMR data from which an entire image can be reconstructed.

To increase the rate at which image frames are acquired, image quality may be sacrificed by acquiring fewer phase encoding views, or by using faster pulse sequences that inherently result in lower quality images. With the spin-warp methods, therefore, there is a trade-off between the number of views that are acquired to achieve the desired image resolution and quality, and the rate at which NMR data for a complete image may be acquired.

Diagnostic studies of the human vasculature have many medical applications. X-ray imaging methods such as digital subtraction angiography ("DSA") have found wide use in the visualization of the cardiovascular system, including the heart and associated blood vessels. Images showing the circulation of blood in the arteries and veins of the kidneys and the carotid arteries and veins of the neck and head have immense diagnostic utility. Unfortunately, however, these x-ray methods subject the patient to potentially harmful ionizing radiation and often require the use of an invasive catheter to inject a contrast agent into the vasculature to be imaged.

Magnetic resonance angiography (MRA) uses nuclear magnetic resonance (NMR) phenomenon to produce images of the human vasculature. Such angiograms provide visualization of the cardiovascular system without subjecting the patient to ionizing radiation. Two basic MRA techniques have been proposed and evaluated. The first class, time-of-flight (TOF) techniques, consists of methods which exploit the differences in signal saturation that exist between flowing blood and stationary tissue. Flowing blood, which is moving through the excited section, is continually refreshed by spins experiencing fewer excitation pulses and is, therefore, less saturated. This effect is magnified by injecting a contrast agent into the patient and timing the acquisition when the contrast bolus flows through the arteries of interest. The result is the desired image contrast between the high-signal blood and the low-signal stationary tissues.

MR methods have also been developed that encode motion into the phase of the acquired signal as disclosed in U.S. Pat. No. Re. 32,701. These form the second class of MRA techniques and are known as phase contrast (PC) methods. Currently, most PC MRA techniques acquire two images, with each image having a different sensitivity to the same velocity component. Angiographic images are then obtained by forming either the phase difference or complex difference between the pair of velocity-encoded images. Phase contrast MRA techniques have been extended so that they are sensitive to velocity components in all three orthogonal directions, but this requires additional data acquisition.

Prevailing MRA techniques employ a method in which k-space is sampled along Cartesian coordinates using a 2DFT or 3DFT fast gradient recalled echo method. While the PC MRA technique does not require the injection of contrast agents into the patient, it is not used in many clinical applications because it usually requires from four to six times as long as the TOF method to acquire the NMR data for a phase contrast MRA image. This is because a separate phase image may be acquired for each axis of motion (x, y and z), and two images (with different velocity encoding) must be acquired for each axis of motion.

The phase contrast technique disclosed in U.S. Pat. No. Re 32,701 is typically used for imaging exams where functional velocity information is desired. It is not usually considered competitive with time of flight (TOF) imaging because the time required for the phase contrast examination is typically four times longer than for TOF assuming the same spatial resolution. In addition, the velocity encoding gradient first moment ("VENC") value must be separately optimized for various vessels that might be present. If the VENC is set too low, high velocities will alias and can give zero signal. If the VENC is set too high, the sensitivity too low velocities will be small. Also, quantitative velocity information usually requires careful selection of an imaging plane perpendicular to the flow so that the in-plane image resolution can be exploited. Typically this is done using 2D slices and the resolution in the slice direction is poor.

U.S. Pat. No. 6,188,922 discloses a method called PIPR which uses undersampled projection imaging in 2-dimensions and Fourier encoding in the third dimension. This technique provides approximately the factor of four reduction in scan time required to catch up in speed with TOF imaging. However, it does not deal with the VENC selection problem or the non-isotropic spatial resolution problems.

The recently developed 3D projection acquisition method called VIPR disclosed in co-pending U.S. patent appln. Ser. No. 09/767,757 filed on Jan. 23, 2001 employs an undersampled projection in three dimensions. This provides greatly increased opportunity for speed increases beyond the hybrid PIPR technique in U.S. Pat. No. 6,188,922.

SUMMARY OF THE INVENTION

The present invention employs a 3D projection reconstruction (3DPR) method for acquiring phase contrast velocity encoded images. By judiciously undersampling the acquisition of velocity encoded components, phase contrast images of isotropic resolution can be acquired in scan times competitive with time of flight (TOF) methods Any angular subset of the fully sampled set of projection angles provides full image resolution aside from some artifacts that are usually acceptable. Because of this an undersampled set of 3DPR data associated with a given velocity direction component and with a given velocity encoding value $M_1$ can be combined with a similar undersampled set of 3DPR data having a different $M_1$ value. A 1D Fourier transformation will generate a set of images corresponding to a spectrum of velocities, one velocity range for each $M_1$ velocity encoding value used during the acquisition.

Not only are all velocities adequately represented, but this approach has the advantage over performing several scans at different $M_1$ values because in this approach all of the acquired signal to noise ratio (SNR) feeds into all of the velocity images due to the 1DFT. An advantage of this is that we no longer have to know the velocity a priori to select the optimal velocity encoding value $M_1$. The velocity in all vessels is adequately represented by a portion of the velocity spectrum. This greatly simplifies the use of phase contrast angiography.

Another advantage of the present invention is that it reduces set up and total scan time. Because of its isotropic resolution, magnet time does not have to be wasted seeking planes perpendicular to the vessels of interest. Instead, the 3D isotropic images can be examined retrospectively to find the vessels of clinical interest. In spite of the added availability of spectral velocity information and high resolution isotropic 3D images, the scan times are essentially the same as for TOF imaging, which does not provide spectral or even single $M_1$ information.

DESCRIPTION OF THE PREFERRED EMBODIMENT

Figure 1:
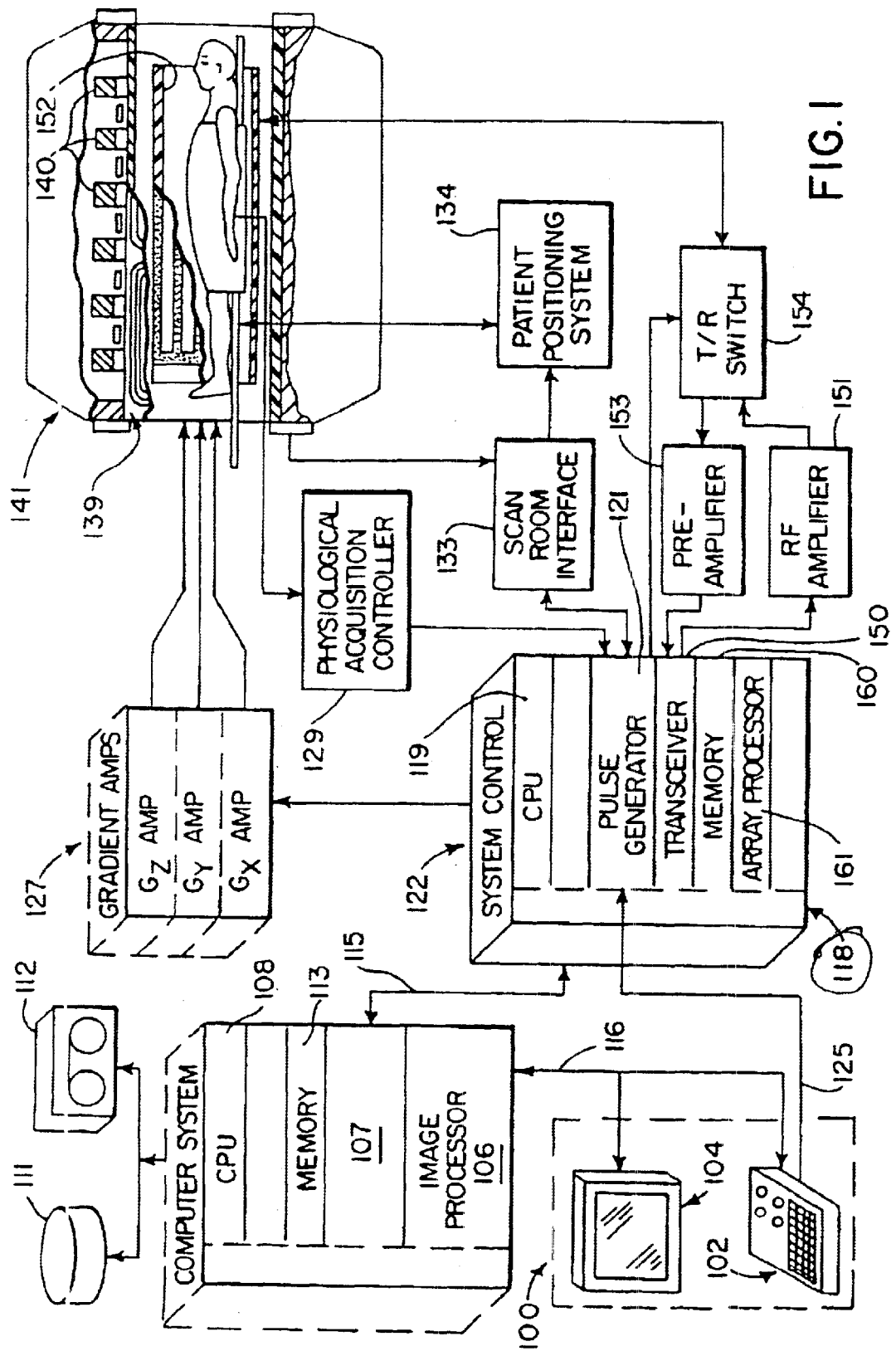
FIG. 1 is a block diagram of an MRI system which employs the present invention.

Referring first to FIG. 1, there is shown the major components of a preferred MRI system which incorporates the present invention. The operation of the system is controlled from an operator console 100 which includes a keyboard and control panel 102 and a display 104. The console 100 communicates through a link 116 with a separate computer system 107 that enables an operator to control the production and display of images on the screen 104. The computer system 107 includes a number of modules which communicate with each other through a backplane. These include an image processor module 106, a CPU module 108 and a memory module 113, known in the art as a frame buffer for storing image data arrays. The computer system 107 is linked to a disk storage 111 and a tape drive 112 for storage of image data and programs, and it communicates with a separate system control 122 through a high speed serial link 115.

The system control 122 includes a set of modules connected together by a backplane. These include a CPU module 119 and a pulse generator module 121 which connects to the operator console 100 through a serial link 125. It is through this link 125 that the system control 122 receives commands from the operator which indicate the scan sequence that is to be performed. The pulse generator module 121 operates the system components to carry out the desired scan sequence. It produces data which indicates the timing, strength and shape of the RF pulses which are to be produced, and the timing of and length of the data acquisition window. The pulse generator module 121 connects to a set of gradient amplifiers 127, to indicate the timing and shape of the gradient pulses to be produced during the scan. The pulse generator module 121 also receives patient data from a physiological acquisition controller 129 that receives signals from a number of different sensors connected to the patient, such as ECG signals from electrodes or respiratory signals from a bellows. And finally, the pulse generator module 121 connects to a scan room interface circuit 133 which receives signals from various sensors associated with the condition of the patient and the magnet system. It is also through the scan room interface circuit 133 that a patient positioning system 134 receives commands to move the patient to the desired position for the scan.

The gradient waveforms produced by the pulse generator module 121 are applied to a gradient amplifier system 127 comprised of Gx, Gy and Gz amplifiers. Each gradient amplifier excites a corresponding gradient coil in an assembly generally designated 139 to produce the magnetic field gradients used for position encoding acquired signals. The gradient coil assembly 139 forms part of a magnet assembly 141 which includes a polarizing magnet 140 and a whole-body RF coil 152. A transceiver module 150 in the system control 122 produces pulses which are amplified by an RF amplifier 151 and coupled to the RF coil 152 by a transmit/receive switch 154. The resulting signals radiated by the excited nuclei in the patient may be sensed by the same RF coil 152 and coupled through the transmit/receive switch 154 to a preamplifier 153. The amplified NMR signals are demodulated, filtered, and digitized in the receiver section of the transceiver 150. The transmit/receive switch 154 is controlled by a signal from the pulse generator module 121 to electrically connect the RF amplifier 151 to the coil 152 during the transmit mode and to connect the preamplifier 153 during the receive mode. The transmit/receive switch 154 also enables a separate RF coil (for example, a head coil or surface coil) to be used in either the transmit or receive mode.

The NMR signals picked up by the RF coil 152 are digitized by the transceiver module 150 and transferred to a memory module 160 in the system control 122 through a backplane 118. When the scan is completed and an entire array of data has been acquired in the memory module 160, an array processor 161 operates to reconstruct one or more images as will be described below. This image data is conveyed through the serial link 115 to the computer system 107 where it is stored in the disk memory 111. In response to commands received from the operator console 100, this image data may be archived on the tape drive 112, or it may be further processed by the image processor 106 and conveyed to the operator console 100 and presented on the display 104.

Figure 2:
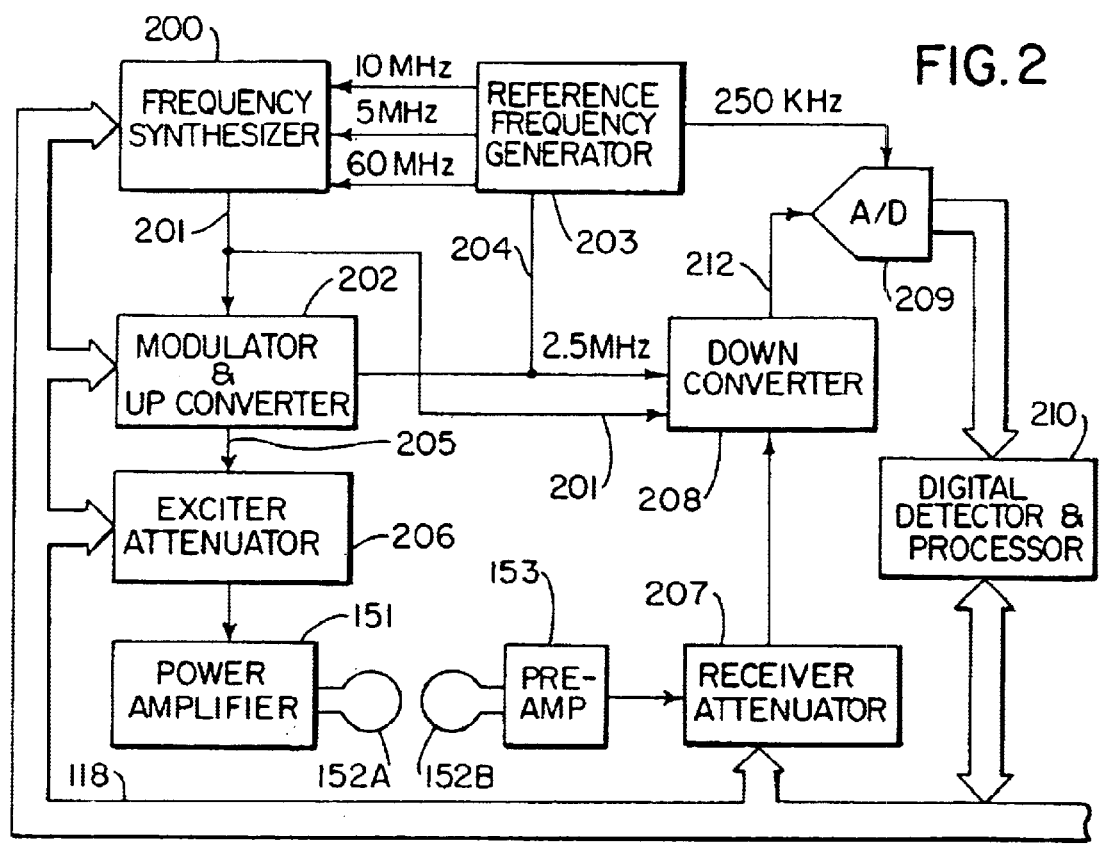
FIG. 2 is an electrical block diagram of the transceiver which forms part of the MRI system of FIG. 1.

Referring particularly to FIGS. 1 and 2, the transceiver 150 produces the RF excitation field B1 through power amplifier 151 at a coil 152A and receives the resulting signal induced in a coil 152B. As indicated above, the coils 152A and B may be separate as shown in FIG. 2, or they may be a single wholebody coil as shown in FIG. 1. The base, or carrier, frequency of the RF excitation field is produced under control of a frequency synthesizer 200 which receives a set of digital signals (CF) from the CPU module 119 and pulse generator module 121. These digital signals indicate the frequency and phase of the RF carrier signal produced at an output 201. The commanded RF carrier is applied to a modulator and up converter 202 where its amplitude is modulated in response to a signal R(t) also received from the pulse generator module 121. The signal R(t) defines the envelope of the RF excitation pulse to be produced and is produced in the module 121 by sequentially reading out a series of stored digital values. These stored digital values may, in turn, be changed from the operator console 100 to enable any desired RF pulse envelope to be produced.

The magnitude of the RF excitation pulse produced at output 205 is attenuated by an exciter attenuator circuit 206 which receives a digital command, TA, from the backplane 118. The attenuated RF excitation pulses are applied to the power amplifier 151 that drives the RF coil 152A. For a more detailed description of this portion of the transceiver 122, reference is made to U.S. Pat. No. 4,952,877 which is incorporated herein by reference.

Referring still to FIGS. 1 and 2 the signal produced by the subject is picked up by the receiver coil 152B and applied through the preamplifier 153 to the input of a receiver attenuator 207. The receiver attenuator 207 further amplifies the signal by an amount determined by a digital attenuation signal (RA) received from the backplane 118.

The received signal is at or around the Larmor frequency, and this high frequency signal is down converted in a two step process by a down converter 208 which first mixes the NMR signal with the carrier signal on line 201 and then mixes the resulting difference signal with the 205 MHz reference signal on line 204. The down converted NMR signal is applied to the input of an analog-to-digital (A/D) converter 209 which samples and digitizes the analog signal and applies it to a digital detector and signal processor 210 which produces 16-bit in-phase (I) values and 16-bit quadrature (Q) values corresponding to the received signal. The resulting stream of digitized I and Q values of the received signal are output through backplane 118 to the memory module 160 where they are employed to reconstruct an image.

The 2.5 MHz reference signal as well as the 250 kHz sampling signal and the 5, 10 and 60 MHz reference signals are produced by a reference frequency generator 203 from a common 20 MHz master clock signal. For a more detailed description of the receiver, reference is made to U.S. Pat. No. 4,992,736 which is incorporated herein by reference.

Figure 4:
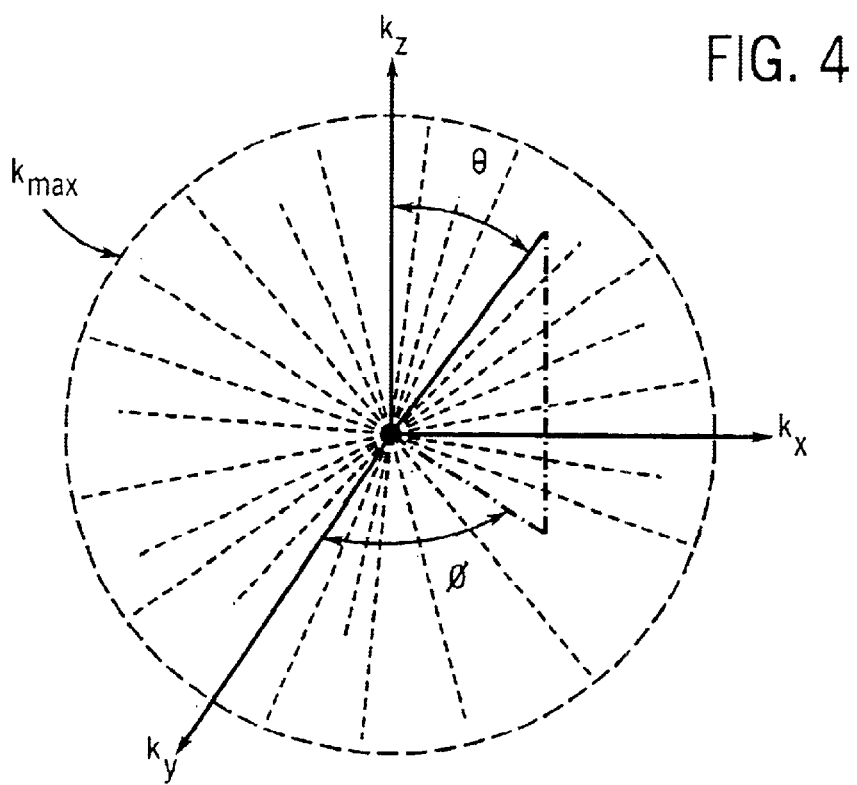

To practice a preferred embodiment of the invention NMR data is acquired in a 3D spherical k-space coordinate system, with the readout gradient direction defined by the angle θ from the kz-axis and by the angle ϕ from the ky-axis, as shown in FIG. 4. The sampling method consists of a series of evenly spaced projections with all projections going through the center of k-space. The maximum k-space radius value (kmax) determines the resolution in all three spatial directions of the resulting image. The radial sample spacing ($\Delta k_r$) determines the diameter (D) of the full field of view (FOV) of the reconstructed image. The full FOV image may be reconstructed without artifacts if the Nyquist condition is met, $\Delta k_\theta$, $\Delta k_\phi \leq k_r$. If this condition is not satisfied, however, alias-free reconstruction still occurs within a reduced diameter (d) that is less than the full FOV (D). If it is assumed that the projections are acquired evenly spaced ($\Delta k_\theta = \Delta k_\phi = \Delta k_r$), then the surface area A at $k_{max}$ associated with a projection is $$A = \Delta k^2 = \frac{2\pi}{N_P} k_{max}^2 \qquad (1)$$

where $N_p$ is the number of acquired views, or projections. Equation (1) determines $\Delta k$, by which the diameter (d) of the reduced FOV due to the angular spacing can be related to the full FOV diameter D as follows:

$$\frac{d}{D} = \frac{2}{N_R}\sqrt{\frac{N_P}{2\pi}}$$

where $N_R$ is the matrix size (i.e. number of samples acquired during the signal readout) across the FOV. In the image domain, a well-constructed reduced FOV appears centered around each object even if the Nyquist condition is not met.

However, radial streak artifacts from outside can enter the local FOV. The condition that k-space be fully sampled, or d=D, requires that the number of sampled projections be:

$$N_P = \frac{\pi}{2} N_R^2. \quad (2)$$

If $N_R$=256 samples are acquired during the readout of each acquired NMR signal, for example, the number of projections $N_p$ required to fully meet the Nyquist condition at the FOV diameter D is around 103,000.

Figure 5:
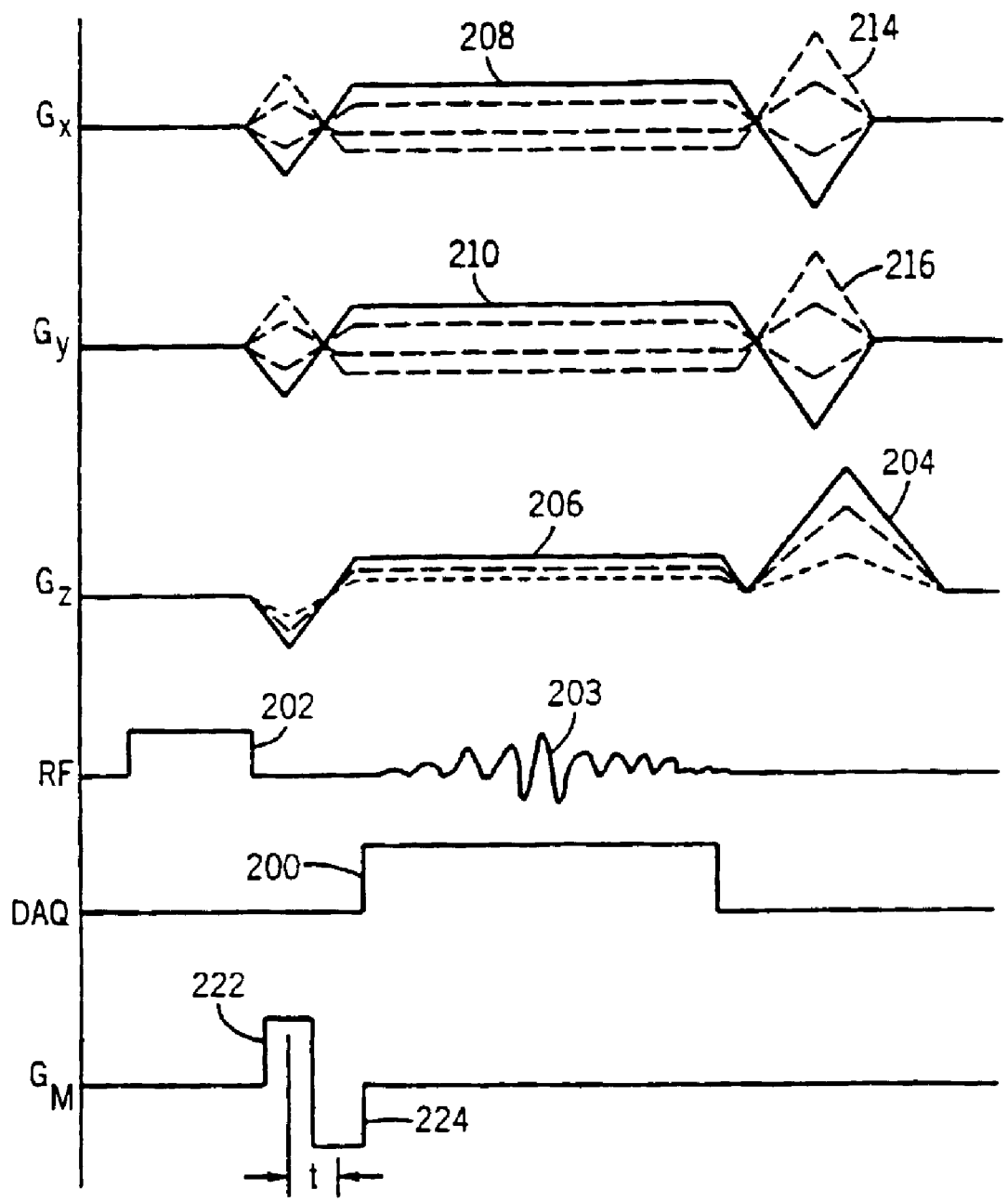
FIG. 5 is a graphic representation of the preferred pulse sequence used by the MRI system of FIG. 1 to practice the present invention.

A pulse sequence used to acquire data as 3D projections is shown in FIG. 5. The sequence is implemented on the above described MRI system equipped with a high-performance gradient subsystem (40 mT/m maximum amplitude and 150 T/m/sec maximum slew rate). Either full-echo or partial-echo readouts can be performed during a data acquisition window 200. If partial echo is chosen, the bottom half of k-space (kz<0) is only partially acquired. Because of the large FOV in all directions, a non-selective 200 ms radio-frequency (RF) pulse 202 can be used to produce transverse magnetization throughout the image FOV. Relative to slab-selective excitation use in conventional spin-warp acquisitions, this method provides a more uniform flip angle across the volume, requires lower RF power, and deposits less energy into the patient.

A gradient-recalled NMR echo signal 203 is produced by spins in the excited FOV and acquired in the presence of three readout gradients 206, 208 and 210. Since a slab-select gradient is not required, the readout gradient waveforms Gx, Gy, and Gz have a similar form. This symmetry is interrupted only by the need to spoil the sequence, which is accomplished by playing a dephasing gradient lobe 204. The area of the dephasing lobe 204 is calculated to satisfy the condition $$\int_0^{T_R} (G_{dephase}(t) + G_{read}(t)) dt = n \cdot k_{max} \quad (3)$$

where n is an integer n≧2. Because the $G_z$ readout gradient 206 is always positive on the logical z-axis, the time required for the spoiling gradient 204 is minimized by playing the dephasing lobe 204 only on $G_z$. The $G_x$ and $G_y$ readout gradients 208 and 210 are rewound by respective gradient pulses 212 and 214 to achieve steady state.

The readout gradient waveforms $G_x$, $G_y$ and $G_z$ are modulated during the scan to sample radial trajectories at different θ and φ angles. The angular spacing of θ and φ are chosen such that a uniform distribution of k-space sample points occurs at the peripheral boundary (kmax) of the sampled k-space sphere. Although several methods of calculating the distribution are known, a method which evenly distributes the projections by sampling the spherical surface with a spiral trajectory, with the conditions of constant path velocity and surface area coverage is used. This solution also has the benefit of generating a continuous sample path, which reduces gradient switching and eddy currents. For the acquisition of N total projections, the equations for the gradient amplitude as a function of projection number n are:

$$G_z = \frac{2n-1}{2N} \quad (4)$$

$$G_x = \cos(\sqrt{2N\pi} \sin^{-1} G_z(n)) \sqrt{1 - G_{z(n)}^2}$$

$$G_y = \sin(\sqrt{2N\pi} \sin^{-1} G_z(n)) \sqrt{1 - G_{z(n)}^2}$$

Each projection number n produces a unique project angle and when this number is indexed from 1 to N during a scan, the spherical k-space is equally sampled along all three axes.

Referring again to FIG. 5, to produce a phase contrast MRA image, each acquired projection is motion sensitized by a bipolar motion encoding gradient $G_M$. As is well known in the art, a velocity encoding gradient $G_M$ is comprised of two gradient lobes 222 and 224 of equal size and opposite polarity. The motion encoding gradient $G_M$ can be applied in any direction and it is played out after transverse magnetization is produced by the RF excitation pulse 202 and before the NMR echo signal 203 is acquired. The motion encoding gradient $G_M$ imposes a phase shift to the NMR signals produced by spins moving in the direction of the gradient $G_M$ and the amount of this phase shift is determined by the velocity of the moving spins and the first moment of motion encoding gradient $G_M$. The first moment ($M_1$) is equal to the product of the area of gradient pulse 222 or 224 and the time interval (t) between them. The first moment $M_1$, which is also referred to as "VENC", is set to provide a significant phase shift, but not so large as to cause the phase to wrap around at high spin velocities.

To ensure that phase shifts in the acquired NMR signals 203 are due solely to spin motion, two acquisitions are commonly made at each projection angle and at each motion encoding gradient value $M_1$. One image acquisition is performed with the bipolar gradient $G_M$ as shown in FIG. 5 and a second image acquisition is made with the polarity of each gradient lobe 260 and 262 reversed. The two resulting phase images are subtracted to null any phase shifts common to both acquisitions. The phase shifts caused by spin motion are also reinforced due to the reversal of motion encoding gradient polarity. An alternative technique is to acquire signals with motion encoding along each axis and then a signal with no motion encoding. The resulting reference velocity image $V_0$ may be subtracted from each of the motion encoded images $V_x$, $V_y$ and $V_z$ to null any phase shifts not caused by spin motion. With this method there is no reinforcement of the phase shifts due to motion.

As indicated above, the motion encoding gradient $G_M$ can be applied in any direction. In the preferred embodiments, the motion encoding gradient $G_M$ is applied separately along each of the gradient axes, x, y and z such that an image indicative of total spin velocity can be produced. That is, an image indicative of velocity along the z axis ($v_z$) is produced by acquiring an image with the bipolar motion encoding gradient $G_M$ added to the $G_z$ gradient waveform shown in FIG. 4, a second velocity image $V_x$ is acquired with the motion encoding gradient $G_M$ added to the $G_x$ gradient waveform, and a third velocity image $V_y$ is acquired with the motion encoding gradient $G_M$ added to the $G_y$ gradient waveform. An image indicative of the total spin velocity is then produced by combining the corresponding pixel values in the three velocity images $$V_T = \sqrt{V_x^2 + V_y^2 + V_z^2}. \quad (7)$$

Figure 7:
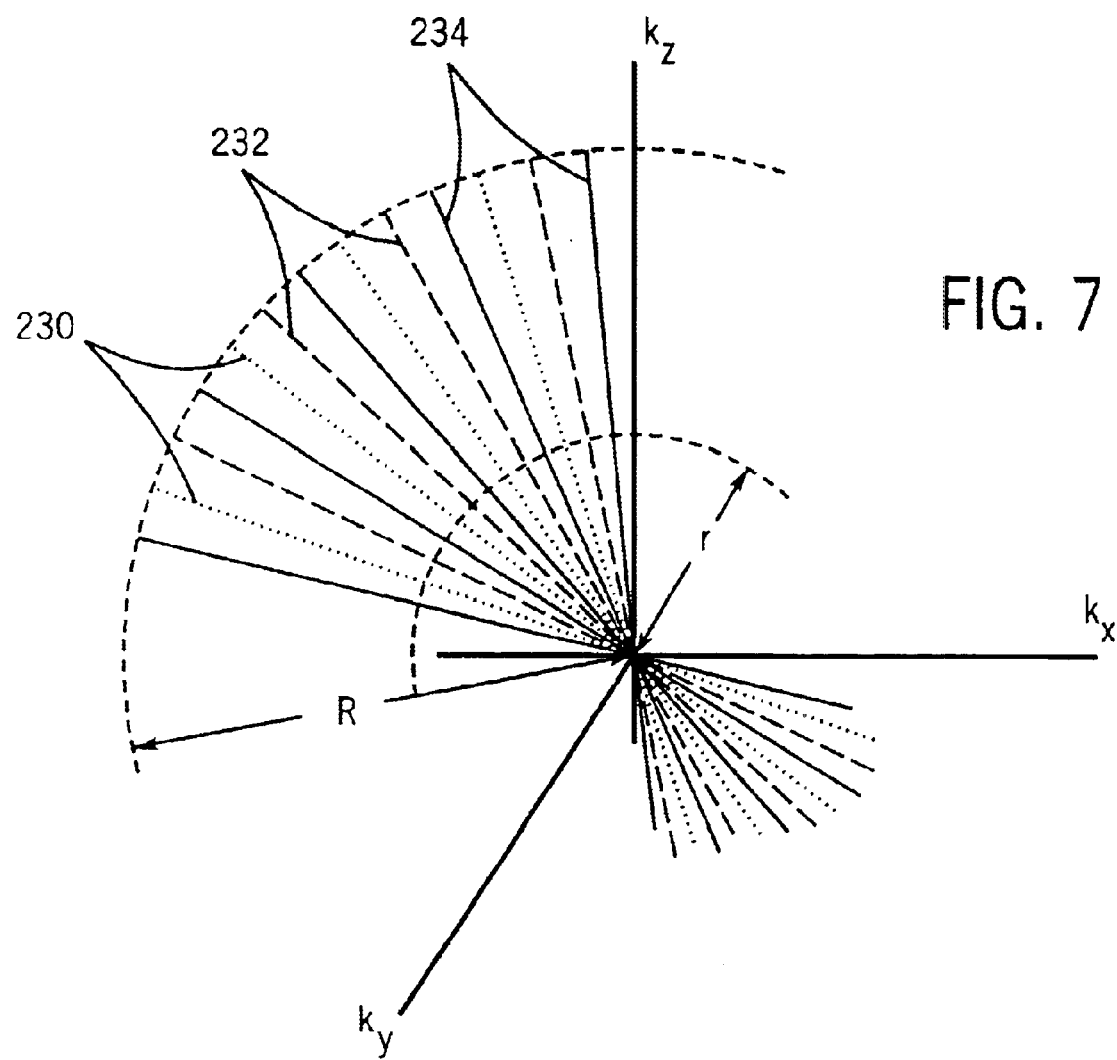
FIG. 7 is a graphical representation of the sets of projections acquired according to another embodiment of the present invention.

The three velocity images $V_x$, $V_y$ and $V_z$ are each undersampled acquisitions that may be acquired at different, interleaved projection angles. This is illustrated for one embodiment in FIG. 7, where projection angles for the velocity image $V_x$ are indicated by dotted lines 230, projection angles for image $V_y$ are indicated by dashed lines 232, and projection angles for image $V_z$ are indicated by lines 234. Each velocity image acquisition samples uniformly throughout the spherical k-space of radius R, but it only fully samples out to a radius r. In this embodiment both a positive and a negative motion encoding of a selected $M_1$ are produced along each axis of motion so that non-motion phase shifts can be subtracted out as discussed above.

Figure 3:
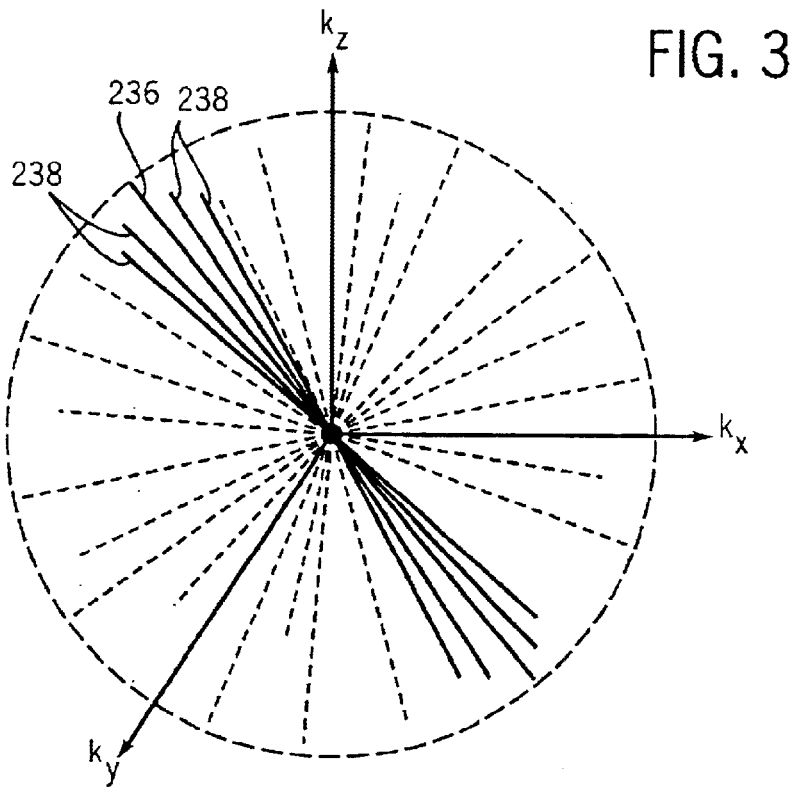
FIGS. 3 and 4 are graphic representations of the sets of projections acquired according to one embodiment of the present invention.

In another embodiment of the present invention not only are interleaved and uniformly spaced projections acquired having different motion encoding gradient $G_M$ directions (i.e., x axis, y axis and z axis), but about each of these is a cluster of projection acquisitions having different motion encoding gradient first moments $M_1$. This is shown in FIG. 3 where each uniformly spaced cluster of projections includes one projection such as that indicated at 236 and a set of surrounding projections 238 having different first moments $M_1$. As discussed above, the different first moments $M_1$ are produced by varying the size or spacing of the motion encoding gradient lobes 222 and 224 in the pulse sequence of FIG. 5. All of these projections contribute to the reduction of streak artifact and at the same time produce a velocity spectrum at each reconstructed 3D image pixel. Assuming a TR of 10 msec for the pulse sequence of FIG. 5, one can collect 24000 projections in a scan of four minutes. This allows acquisition of 8 different velocity encoding projections 238 in each of three flow directions in the immediate vicinity of 1000 central, uniformly spaced, projections 236.

In yet another embodiment of the invention four different velocity encoded images are acquired using four different positive motion encoding gradients ($M_1$=1, 2, 3, 4) and their four inverses ($M_1$=−1, −2, −3, −4). In this case N is set to 1000 in the above equations (4), (5) and (6), and at each of the 1000 projection angles (n), these eight different velocity encoded projections are acquired. They are acquired in the order $M_1$=1, −1, 2, −2, 3, −3, 4, −4 so that corresponding pairs of velocity encoded signals are acquired as close as possible in time to each other. In this embodiment no $M_1$=0 signal is acquired and a four minute scan can acquire the eight velocity encoded images as in the previous embodiment. When the pairs of images are subtracted to eliminate non-motion phase shifts, four velocity images of different $M_1$ velocity encoding are produced.

It can be appreciated by those skilled in the art that data is acquired in the above embodiments to produce from one to four velocity images, but that the particular number of images acquired is a matter of choice. The choice will usually be dictated by the particular clinical application.

Another aspect of the present invention is to use available scan time to acquire a series of velocity images depicting the subject at successive functional phases. For example, a series of 3D velocity images of the heart may be acquired and reconstructed which depict the heart at successive cardiac phases.

Figure 8:
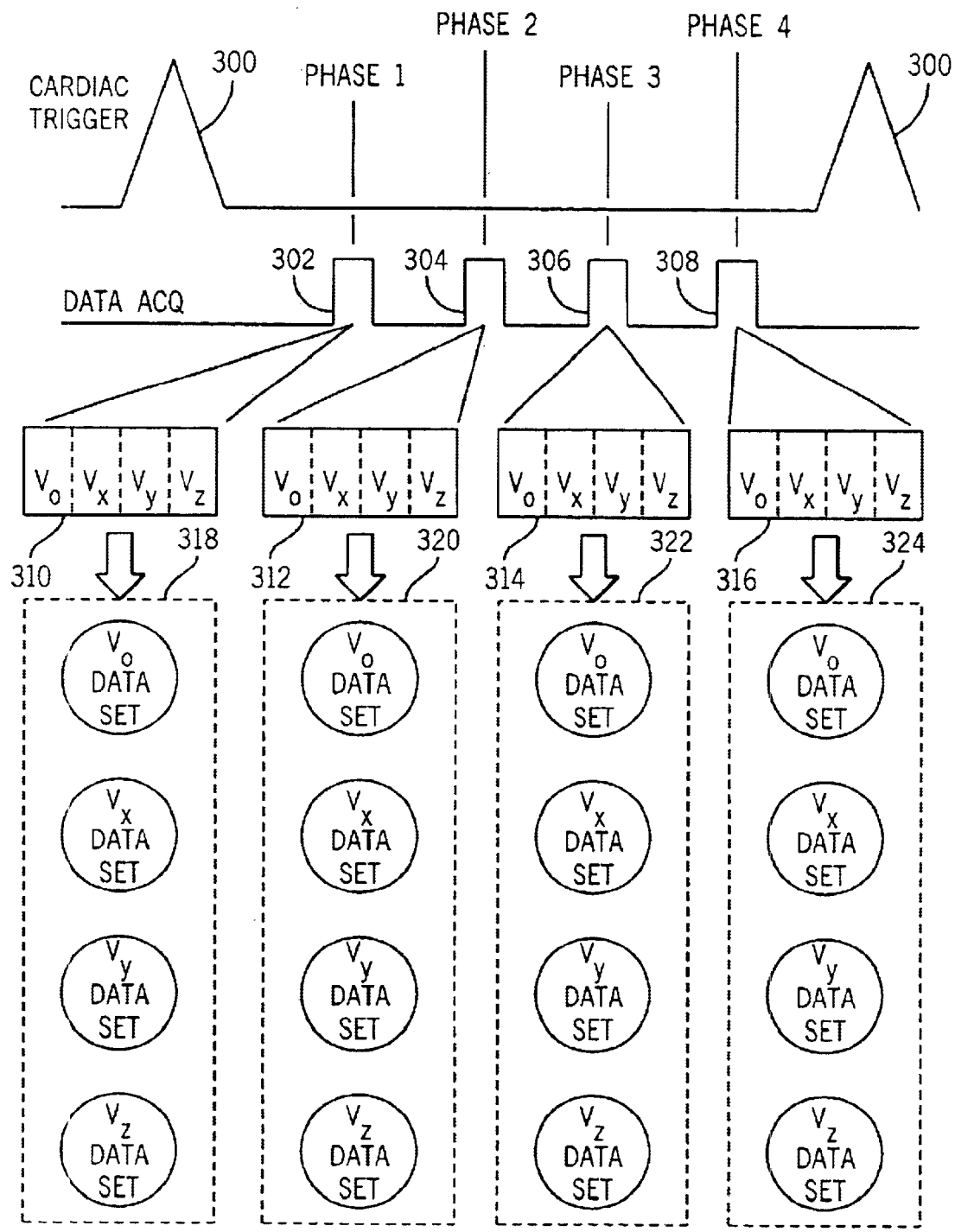
FIG. 8 is a graphic representation of the data acquisition sequence according to another embodiment of the invention using the MRI system of FIG. 1.

Referring particularly to FIG. 8, in this embodiment the projections are acquired during the interval between cardiac trigger signals 300 produced by an ECG monitor attached to the subject. This "R—R" interval is divided into four phases during which four corresponding segments 302, 304, 306 and 308 of projection data are acquired. During each segment 302-308 four projections are acquired as indicated at 310, 312, 314, and 316. The first projection has no velocity encoding (M1=0) and the remaining three projections are velocity encoded along the respective x, y and z axis at a preselected value of $M_1$. The projection angle remains fixed for all acquisitions during a single heart beat. The projection angle (n) is changed after each heart beat in accordance with the above equations (4), (5) and (6) where N=1000. However, n is increased by 4 after each heart beat and when n reaches N after 250 heart beats, the cycle is repeated three more times starting at n=2, n=3 and n=4, respectively, to sample all the skipped projection angles n. Thus, although 1000 projection acquisitions are made for each image, the 3D spherical k-space is substantially uniformly sampled every 250 projection acquisitions. If the patient moves during the scan, this "time interleaved" acquisition sequence enables an acceptable, but undersampled image to be produced with as few as 250 acquisitions.

At the completion of 1000 heart beats, sixteen k-space image data sets have been acquired. Four data sets 318 of 1000 projections each have been acquired during cardiac phase 1, four data sets 320 have been acquired during cardiac phase 2, four data sets 322 have been acquired during cardiac phase 3, and four data sets 324 have been acquired during cardiac phase 4. One data set $V_0$ at each cardiac phase has no motion encoding ($M_1$=0) and the remaining data sets $V_x$, $V_y$, $V_z$ at each cardiac phase are motion encoded along the respective x, y and z axes with the same preselected first moment $M_1$.

It can be appreciated that many variations are possible from this preferred embodiment of the cardiac gated acquisition method. The number of cardiac phases which are acquired may be changed and the total number of projection acquisitions acquired during the scan may be changed depending on the condition of the patient. Also, rather than acquiring four projections with motion encoding as described above, six projections with positive x, y and z motion encoding and negative x, y and z motion encoding may be acquired.

It is also possible to use retrospective cardiac gating rather than prospective cardiac gating as described above. In this case the four projections $V_0$, $V_x$, $V_y$ and $V_z$ are acquired continuously during each cardiac cycle and each acquired projection is tagged with cardiac phase data indicating when it was acquired during the R—R interval. The projection angle remains the same throughout each cardiac cycle and the acquired projections can be retrospectively grouped into cardiac phases using the cardiac phase tag data. This retrospective cardiac gated method offers the possibility of acquiring more cardiac phase images than the prospective method.

The processing of the velocity encoded projection data sets acquired using one of the above-described acquisition methods will, of course, vary somewhat depending on the particular acquisition method used and the particular clinical images that are sought. This will now be described with reference to FIGS. 6, 9, 10 and 11.

Figure 6:
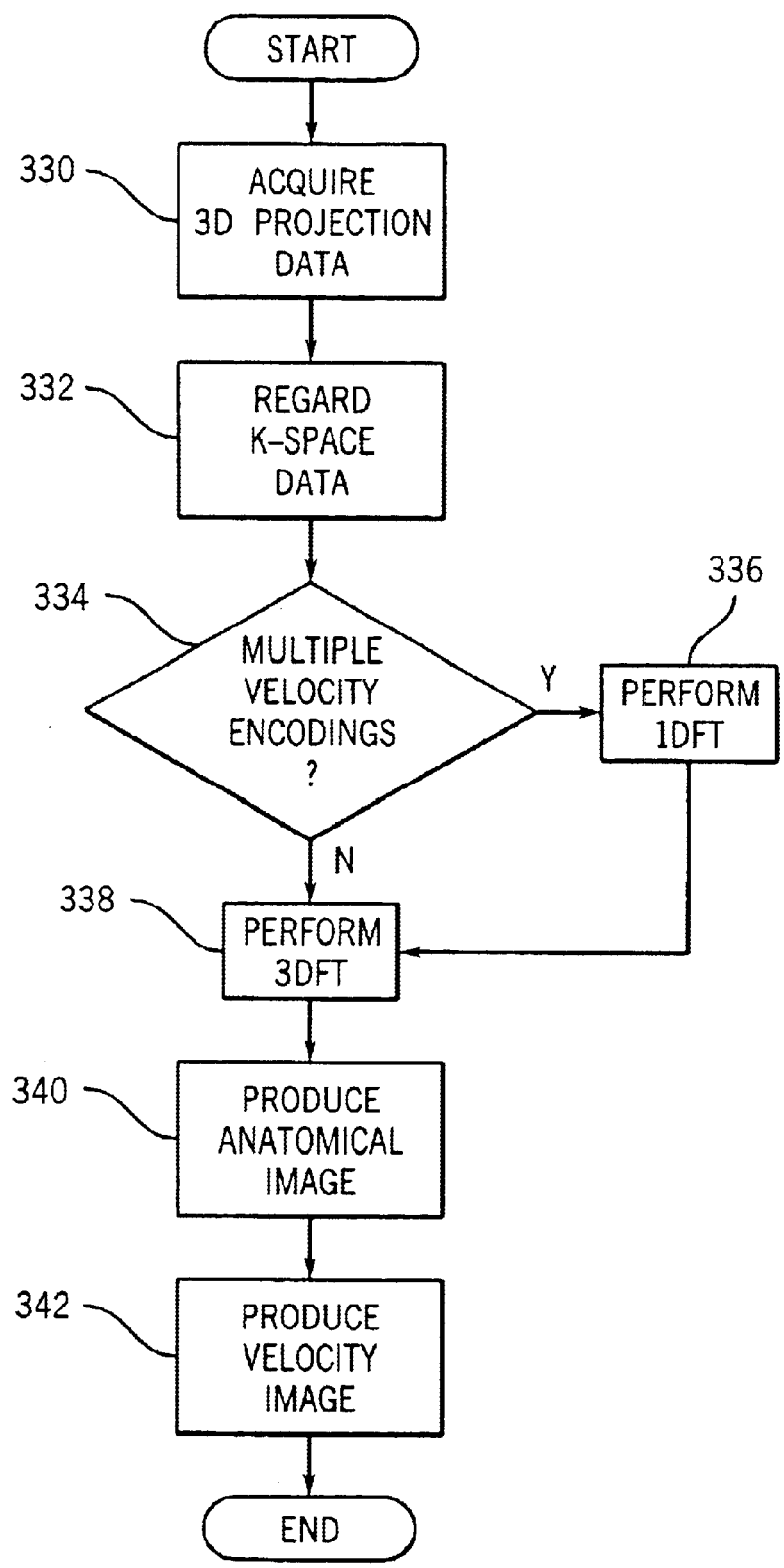
FIG. 6 is a flow chart of the preferred embodiment of the invented method practiced on the MRI system of FIG. 1.
Figure 9:
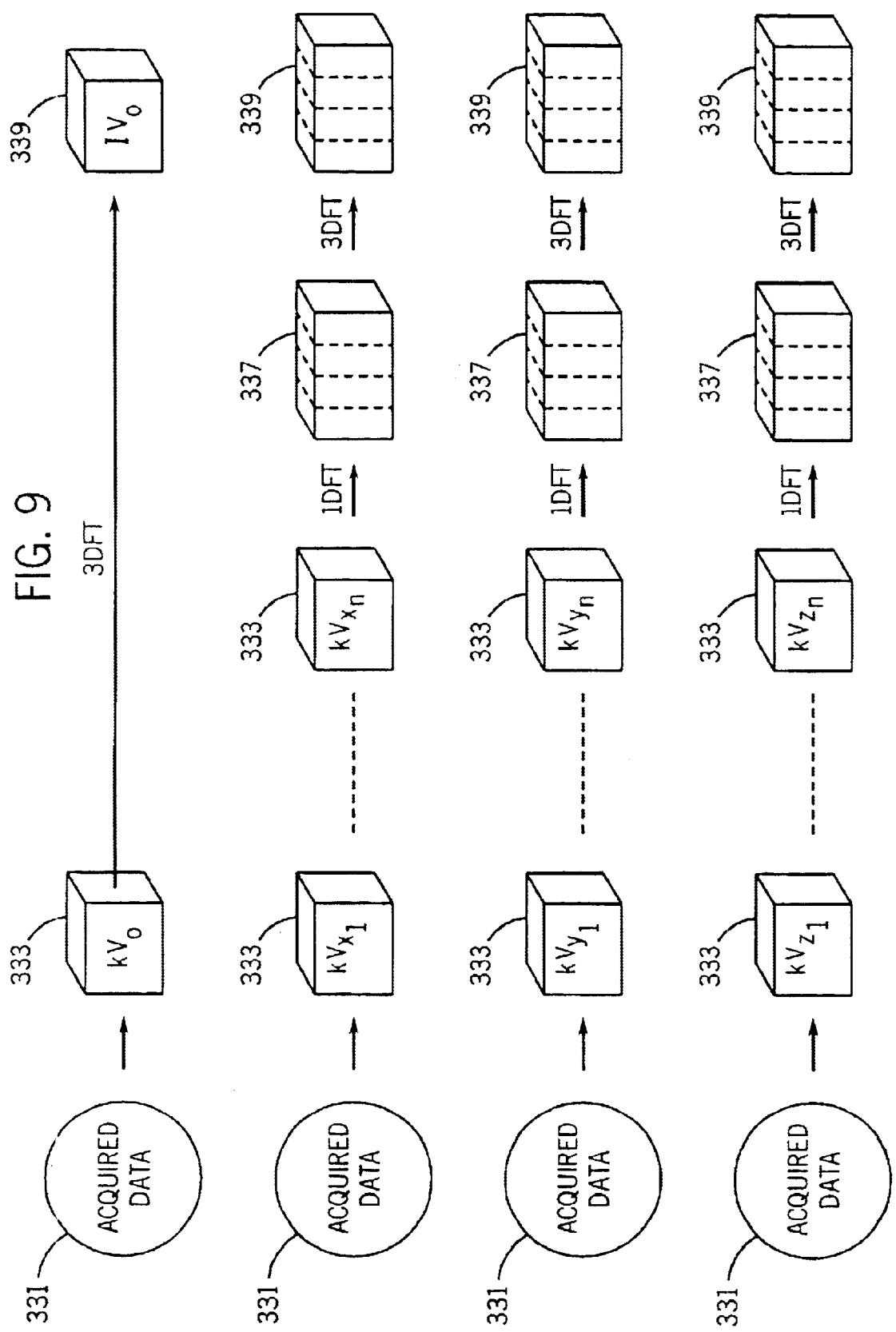
FIG. 9 is a pictorial representation of data structures produced when practicing preferred embodiments of the invention.

Referring particularly to FIGS. 6 and 9, after the velocity encoded projection data sets are acquired as indicated at process block 330, they are saved in raw, k-space image data sets 331 and then regridded as indicated at process block 332. Regridding places the acquired data set on a 3D Cartesian grid. Such regridding methods are well known in the art and is described, for example, in J. Jackson et al, "Selection Of Convolution Function For Fourier Inversion Using Gridding," *IEEE Trans. Med. Imaging*, 10, 473–478, 1991. Each resulting 3D array 333 of k-space data are density compensated with a $\rho^2$ filter, where $\rho$ is the k-space radius of the data point being compensated. The $\rho$=0 point is weighted according to the finite sphere of volume that it samples, similar to the correction proposed for 2D projection filters. The kernel used for the regridding process is either a simple triangle function, which is computationally very fast, or a Kaiser-Bessel function, which has the advantage of reducing aliased energy from the regridding process.

If multiple velocity encodings were acquired along each axis as determined at decision block 334, there are multiple k-space data sets for each axis:

$kV_{x1}, kV_{x2} \ldots KV_{xm}$ $kV_{y1}, kV_{y2} \ldots kV_{ym}$ $kV_{z1}, kV_{z2} \ldots kV_{zm}$ where 1, 2, . . . m indicates the amount of velocity encoding $M_1$ employed.

On the other hand, in some of the above-described acquisition methods only a single velocity encoding is employed for each axis and one of the following sets of 3D k-space data is acquired:

$kV_0$, $kV_x$, $kV_y$, $kV_z$ or $+kV_x$, $-kV_x$, $+kV_y$, $-kV_y$, $+kV_z$, $-kV_z$ where $kV_0$ is a reference k-space data set acquired with M1=0. In this case, each 3D k-space data set 333 is Fourier transformed as indicated at process block 338 to produce corresponding 3D image space data sets 339.

When multiple velocity encodings have been employed as determined at decision block 334, a one-dimensional complex fast Fourier transformation is performed along the velocity encoding axis as indicated at process block 336. As shown in FIG. 9, this 1DFT produces corresponding sets of 3D k-space data 337 which are sorted into velocity bins along each axis, x, y and z. For example, if eight different velocity encodings M1 are used, eight different velocity bin k-space data sets 337 are produced. Each velocity bin covers a different range of spin velocities.

In the embodiment described above in which four positive motion encoding gradients ($M_1$=1, 2, 3, 4) and their four inverses ($M_1$=−1, −2, −3, −4) are acquired it is preferred to subtract the four inverse k-space data sets 331 from their corresponding positive velocity encoded k-space data sets 331 before the regridding and 1DFT steps are performed. This results in four subtracted k-space data sets which in turn produce four velocity bin k-space data sets 337 rather than eight bins.

As indicated by process block 338, the 3D k-space data 337 is then Fourier-transformed in all three directions to produce corresponding 3D image space data sets 339. This is a complex fast Fourier transformation and it produces complex values I and Q at each voxel, or pixel, in the 3D image space data sets 339. For multiple velocity encoding acquisitions this results in the following 3D image data sets:

$IV_{x1}$, $IV_{x2}$ ... $IV_{xm}$ $IV_{y1}$, $IV_{y2}$ ... $IV_{ym}$ $IV_{z1}$, $IV_{z2}$ ... $IV_{zm}$ where 1, 2 ... m indicate a velocity range, or "bin" produced by the IDFT along the velocity encoding axes. When single velocity encodings are employed during the acquisition, one of the following 3D image data sets result:

$IV_0$, $IV_x$, $IV_y$, $IV_z$ or $+IV_x$, $-IV_x$, $+IV_y$, $-IV_y$, $+IV_z$, $-IV_z$.

As indicated by process blocks 340 and 342, a number of different anatomical images and velocity images are then produced from these 3D image data sets.

Figure 10:
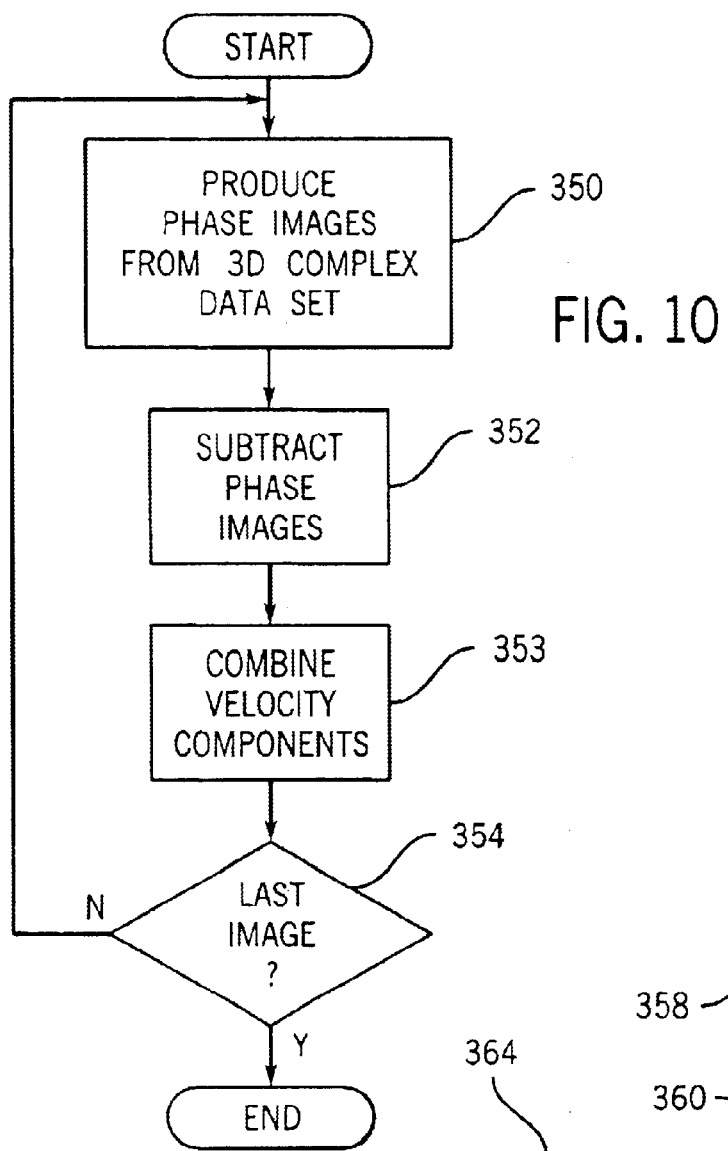
FIG. 10 is a flow chart depicting the steps for producing velocity images which forms part of the method of FIG. 6.

Referring particularly to FIG. 10, one or more velocity images may be produced depending on the particular data acquisition method used. In any case the first step as indicated by process block 350 is to calculate a phase image from each 3D complex image data set 339. This is done by calculating the phase $\phi$ from the complex values I and Q at each image pixel:

$$\phi = \tan^{-1} I/Q. \qquad (8)$$

As indicated at process block 352, the next step is to subtract out phase shifts caused by factors other than spin motion. In the above-described acquisition in which pairs of oppositely motion encoded data sets are acquired, the two phase images resulting from each pair are subtracted from each other. On the other hand, if the acquisition method employs a motion compensated, reference data set with no motion encoding, the reference phase image is subtracted from each of the three phase images produced from the motion encoded data sets ($IV_x$, $IV_y$, $IV_z$). Regardless of the exact method used, three phase images which indicate velocity $V_x$, $V_y$ and $V_z$ along the respective x, y and z axes are produced.

While these velocity component images $V_x$, $V_y$ and $V_z$ are preferably viewed separately, it is also possible to combine the velocity components as indicated at process block 353. This is done as set forth above in equation (7) by calculating the square root of the sum of the squares of the velocity components. The resulting motion encoded images may be displayed or stored for later use. This process continues until all the motion encoded images are produced as determined at decision block 354.

When a multiple velocity encoded acquisition is performed multiple 3D velocity images are produced for each axis of motion encoding. There are a number of ways to combine the corresponding velocity values in each of these velocity bins, but in the preferred embodiment the maximum velocity value is selected for a composite velocity component image. That is the velocity values in each bin are examined for each pixel, and the largest value is chosen. This is done for each axis of motion to form three composite velocity component images $V_x$, $V_y$ and $V_z$ which can be viewed separately or combined in accordance with equation (7).

Figure 11:
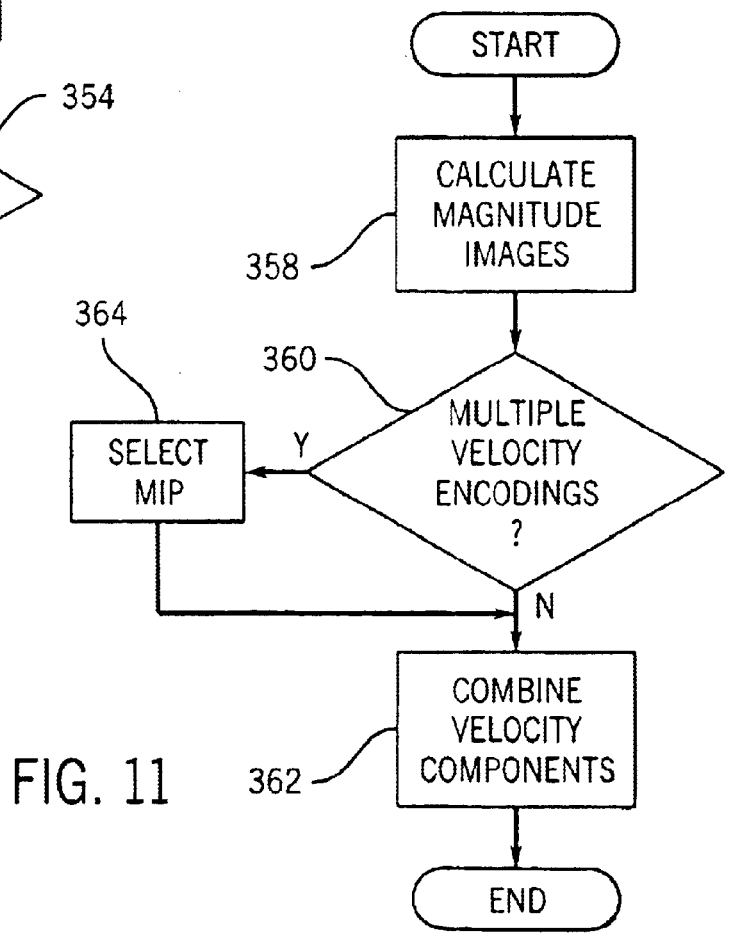
FIG. 11 is a flow chart depicting the steps for producing anatomical images which forms part of the method of FIG. 6.

Referring particularly to FIG. 11, anatomical images may also be produced from the acquired data. As indicated at process block 358, the first step is to calculate a magnitude image from each 3D complex image data set 339. This is done by calculating the magnitude MV from the complex values I and Q at each image voxel:

$$MV = \sqrt{I^2 + Q^2}. \qquad (9)$$

When only a single velocity encoded image data set is acquired (i.e., either $IV_0$, $IV_x$, $IV_y$, $IV_z$ or $+IV_x$, $-IV_x$, $+IV_y$, $-IV_y$, $+IV_z$, $-IV_z$) as determined at decision block 360, the resulting magnitude images are combined as follows at process block 362 to produce the final magnitude image:

$$M_{total} = \sqrt{(MV_x - MV_0)^2 + (MV_y - MV_0)^2 + (MV_z - MV_0)^2} \qquad (10)$$

or $$M_{total} = \sqrt{(^+MV_x - {}^-MV_x)^2 + (^+MV_y - {}^-MV_y)^2 + (^+MV_z - {}^-MV_z)^2} \qquad (11)$$

The resulting magnitude image is either displayed or saved for later use.

When multiple velocity encodings were applied during the data acquisition phase as determined at decision block 360, a unique velocity maximum intensity pixel image is produced from the multiple $IV_x$, $IV_y$ and $IV_z$ velocity bin images 339. For each axis of motion encoding (x, y and z), and for each image pixel, the corresponding image pixel is examined in each velocity bin. The maximum intensity pixel is selected from these bins at process block 364 and combined with the other maximum intensity pixels to form respective magnitude images $MV_x$, $MV_y$ and $MV_z$. These are combined at process block 362 using the above equation (10).

This invention describes high-speed methods for 3D phase contrast magnetic resonance imaging. The methods are based on a highly undersampled 3D projection acquisition in which separate velocity encodings are acquired at the same or slightly different sets of interleaved angular projection positions. In its simplest form it provides a 3D phase contrast examination in times comparable to or faster than time of flight examinations of comparable spatial resolution. The high speed of the examination can also be used to provide prospective or retrospective ECG gated acquisitions to provide for phase contrast measurements of velocity waveforms within the cardiac cycle. Additionally, several different velocity encodings can be placed at different projection angles in order to provide velocity spectral information within each voxel. The information within each voxel can be processed to ensure that an optimal velocity encoding value has been chosen for each voxel. This removes a significant uncertainty associated with phase contrast imaging.

What is claimed is:

1. A method for producing a magnetic resonance image indicative of spin motion, the steps comprising:

a) acquiring an NMR signal with an MRI system using a three-dimensional projection reconstruction pulse sequence which includes:

producing an RF excitation field;

producing a motion encoding gradient field $G_M$ directed along a motion encoding axis; and acquiring an NMR signal while producing a readout gradient to sample a three-dimensional k-space volume along a trajectory that extends substantially radially from the center of k-space;

b) producing a first k-space data set by repeating step a) using different readout gradients to sample k-space throughout the three-dimensional k-space volume along different trajectories with substantially uniform spacing between trajectories;

c) producing a second k-space data set by repeating steps a), and b) using a different motion encoding gradient $G_M$;

d) reconstructing a first phase image from the first k-space data set;

e) reconstructing a second phase image from the second k-space data set;

f) producing a velocity image by combining the first and second phase images, in which the initial motion encoding gradient field $G_M$ has a first moment +M1 and the second motion encoding gradient field $G_M$ has an opposite first moment −M1 and step f) is performed by subtracting the first and second phase images; and which includes repeating steps a)–c) a plurality of times using motion encoding gradient fields $G_M$ having different valued first moments +M1 and −M1 for each repeat, producing a corresponding plurality of first k-space data sets and a corresponding plurality of second k-space data sets, and wherein step f) includes subtracting corresponding k-space data sets in said plurality of first and second k-space data sets to form a plurality of subtracted k-space data sets, and performing a one-dimensional Fourier transformation along corresponding locations in the plurality of subtracted k-space data sets to produce velocity bin data sets.

2. The method as recited in claim 1 which step f) includes selecting values from the velocity bin data sets to produce the velocity image.

3. A method for producing images indicative of spin motion at different phases of a cardiac cycle, the steps comprising:

a) producing a gating signal which indicates the different cardiac phases;

b) acquiring an NMR signal with an MRI system using a three-dimensional projection reconstruction pulse sequence which is performed during each of the indicated cardiac phases by:

producing an RF excitation field;

producing a motion encoding gradient field $G_M$ directed along a first motion encoding axis; and acquiring an NMR signal while producing a readout gradient to sample a three-dimensional k-space volume along a trajectory that extends substantially radially from the center of k-space;

c) producing a first k-space data set for each cardiac phase by repeating step b) using a different readout gradient to sample a three-dimensional k-space volume with substantially uniform spacing between trajectories; and d) reconstructing a velocity image from each of said first k-space data sets.

4. The method as recited in claim 3 which includes:

e) producing a second k-space data set for each cardiac phase by performing steps b) and c) using a different motion encoding gradient field $G_M$ directed along a second motion encoding axis which is perpendicular to said first motion encoding axis; and wherein step d) includes reconstructing a second velocity image from each of said second k-space data sets.

5. The method as recited in claim 4 which includes:

f) producing a third k-space data set for each cardiac phase by performing steps b) and c) using a different motion encoding gradient field $G_M$ directed along a third motion encoding axis which is perpendicular to said first and second motion encoding axes; and wherein step d) includes reconstructing a third velocity image from each of said third k-space data sets.

6. The method as recited in claim 5 in which step d) includes:

d)i) regridding the first, second and third k-space data sets to form rectilinear first, second and third k-space data sets;

d)ii) Fourier transforming the first, second and third sets of rectilinear k-space data sets to form first, second and third sets of image data sets;

d)iii) calculating first, second, and third sets of velocity component images from the corresponding first, second, and third image data sets; and d)iv) combining corresponding velocity component images in aid first, second and third sets of velocity component images to form said velocity images.

7. The method as recited in claim 6 which includes:

g) producing a reference k-space data set for each cardiac phase by performing steps b) and c) with substantially no motion encoding gradient $G_M$;

h) regridding the reference k-space data sets;

i) Fourier transforming the regridded reference k-space data sets; and j) calculating a set of reference phase images from the Fourier transformed reference k-space data sets; and wherein step d)iii) includes calculating first, second and third sets of phase images from the corresponding first, second and third image data sets and subtracting respective reference phase images from corresponding phase images in said first, second and third sets of phase images.

8. The method as recited in claim 3 in which step c) is performed by repeatedly under sampling the three-dimensional k-space volume over a plurality of successive cardiac cycles, and each repeated under sampling being performed with a corresponding plurality of trajectories that are interleaved with the trajectories for the other under samplings.

9. A method for producing an image indicative of the velocity of moving spins in a subject, the steps comprising:
   a) acquiring a first k-space data set with a magnetic resonance imaging system which repeatedly performs a three-dimensional projection reconstruction pulse sequence that includes:
   a)i) producing an RF excitation field;
   a)ii) producing a motion encoding gradient field $G_M$ directed long a first motion encoding axis and having a first moment M1 of a first selected value;
   a)iii) acquiring an NMR signal while producing a readout gradient to sample a three-dimensional k-space volume along a trajectory that extends sustantially radially from the center of k-space;
   a)iv) repeating steps a)i), a)ii) and a)iii) a plurality of times using different readout gradients to sample the three-dimensional k-space volume substantially uniform in all directions from the center of k-space;
   b) acquiring a second k-space data set by repeating step a) using a motion encoding gradient field $G_M$ directed along a second motion encoding axis which is perpendicular to the first motion encoding axis;
   c) reconstructing a first velocity component image from the first k-space data set;
   d) reconstructing a second velocity component image from the second k-space data set;
   f) acquiring a plurality of first k-space data sets by repeating step a) a corresponding plurality of times, each repeat using a motion encoding gradient field $G_M$ having a different value for the first moment M1;
   g) acquiring a plurality of second k-space data sets by repeating step b) a corresponding plurality of times, each repeat using a motion encoding gradient field $G_M$ having a different value for the first moment M1; and in which
   step c) includes performing a one-dimensional Fourier transformation along corresponding locations in said plurality of first k-space data sets; and
   step d) includes performing a one-dimensional Fourier transformation along corresponding locations in said plurality of second k-space data sets.

10. The method as recited in claim 9 which the readout gradients produced during step b) are different from those produced during step a) such that the sampling trajectories in step b) are interleaved with the sampling trajectories in step a).

11. The method as recited in claim 9 in which the readout gradients produced during steps f) and g) are different for each motion encoding gradient field first moment value such that the sampling trajectories for the plurality of first k-space data sets are interleaved with each other and the sampling trajectories of the plurality of second k-space data sets are interleaved with each other.

* * * * *

UNITED STATES PATENT AND TRADEMARK OFFICE
CERTIFICATE OF CORRECTION

PATENT NO.    : 6,954,067 B2
DATED         : October 11, 2005
INVENTOR(S)   : Charles A. Mistretta It is certified that error appears in the above-identified patent and that said Letters Patent is hereby corrected as shown below:

Column 15,
Line 23, "directed long a" should be -- directed along a --.
Line 27, "sustantially" should be -- substantially --.

Signed and Sealed this

Twenty-fourth Day of January, 2006

JON W. DUDAS
*Director of the United States Patent and Trademark Office*

UNITED STATES PATENT AND TRADEMARK OFFICE
CERTIFICATE OF CORRECTION

PATENT NO. : 6,954,067 B2
APPLICATION NO. : 10/290735
DATED : October 11, 2005
INVENTOR(S) : Charles A. Mistretta Page 1 of 1

It is certified that error appears in the above-identified patent and that said Letters Patent is hereby corrected as shown below:

In the Specification

Column 1, Lines 16-19:
Delete the phrase:
"This invention was made with government support under Grant No. HL62425 awarded by the National Institute of Health. The United States Government has certain rights in this invention."

And replace with:
--This invention was made with government support under HL062425 awarded by the National Institutes of Health. The government has certain rights in the invention.--.

Signed and Sealed this
Fifteenth Day of December, 2020

Andrei Iancu
*Director of the United States Patent and Trademark Office*